United States Patent
Nideborn Wärnå et al.

(10) Patent No.: US 7,945,328 B2
(45) Date of Patent: May 17, 2011

(54) STRAIN RELIEVER FOR A LEAD OF AN IMPLANTABLE HEART STIMULATOR

(75) Inventors: Maria Nideborn Wärnå, Järfälla (SE); Per Jarl, Järfälla (SE); Paul Leone, Järfälla (SE); Mikael Sjögren, Fjärdhundra (SE)

(73) Assignee: St. Jude Medical AB, Jarfalla (SE)

( * ) Notice: Subject to any disclaimer, the term of this patent is extended or adjusted under 35 U.S.C. 154(b) by 623 days.

(21) Appl. No.: 12/093,782

(22) PCT Filed: Nov. 30, 2005

(86) PCT No.: PCT/SE2005/001809
§ 371 (c)(1),
(2), (4) Date: May 15, 2008

(87) PCT Pub. No.: WO2007/064262
PCT Pub. Date: Jun. 7, 2007

(65) Prior Publication Data
US 2008/0288014 A1   Nov. 20, 2008

(51) Int. Cl.
*A61N 1/372* (2006.01)
(52) U.S. Cl. .......................................................... 607/37
(58) Field of Classification Search ............... 607/36–37
See application file for complete search history.

(56) References Cited

U.S. PATENT DOCUMENTS

| | | | |
|---|---|---|---|
| 4,944,088 A | 7/1990 | Doan et al. | |
| 4,995,389 A | 2/1991 | Harris | |
| 5,433,734 A | 7/1995 | Stokes et al. | |
| 5,676,694 A | 10/1997 | Boser et al. | |
| 5,954,759 A | 9/1999 | Swoyer et al. | |
| 2003/0073348 A1 | 4/2003 | Ries et al. | |

FOREIGN PATENT DOCUMENTS

DE   103 17 867   10/2004

*Primary Examiner* — Scott M Getzow
*Assistant Examiner* — Amanda Patton
(74) *Attorney, Agent, or Firm* — Schiff Hardin LLP

(57) ABSTRACT

A strain reliever for a lead of an implantable heart stimulator, the lead including at least one cable having an electric conductor, has a body of electrically conducting material in electric contact with the electric conductor. The body is lockable in a position in electric contact with electric circuitry of the heart stimulator. The body has a fastening arrangement for fastening the proximal end of the cable at the fastening point on the peripheral surface of the body located at a distance from the distal end of the body. A fixing arrangement is provided at the distal end of the body for fixing the cable to extend in the distal direction from a departure point at the body distal end. The cable is intended to extend in a helical path on the peripheral surface of the body between the fastening point and the departure point.

13 Claims, 2 Drawing Sheets

STRAIN RELIEVER FOR A LEAD OF AN IMPLANTABLE HEART STIMULATOR

BACKGROUND OF THE INVENTION

1. Field of the Invention

The present invention relates to a strain reliever for a lead of an implantable heart stimulator, said lead including at least one electric cable having an electric conductor, and said strain reliever comprising a body of electrically conducting material in electric contact with the electric conductor, which body is lockable in a position in electric contact with electric circuitry of the heart stimulator.

2. Description of the Prior Art

When applying a pulling force to a conventional heart stimulator lead having coil conductors part of the pulling force is absorbed by the coils, however, the weld joint of the conductors to connector pins have appeared to be weak points with an apparent risk of breakage. To try to reduce this risk of breakage different strain relief means have been suggested. In e.g. U.S. Pat. No. 5,433,734 a strain relief collar of for instance silicon rubber is described. The collar is surrounding the connector pin and the terminal end of the lead. Another example is disclosed in United States Patent Application Publication 2004/0106964 wherein a strain relief tube which is mounted on a connector unit of a heart stimulator couples the lead body to this connector unit.

In new lead technology the coil conductor is often replaced by a cable having a straight electric conductor. Such a lead structure will make the lead body stiff in longitudinal direction and a pulling force in the lead will be applied practically in its entirety to the weld joint of the lead to the connector pin or ring.

The risk of breakage at the point where the cable is welded, at the connector end of the lead, is thus increased in this new lead structure. For an example of such a new lead structure the force needed to break the cable itself is more than 30 N, whereas a force of about 17 N has appeared to be sufficient for breaking the weld.

SUMMARY OF THE INVENTION

An object of the present invention is to provide a solution to this problem that provides a sufficient strain relief at the proximal end of such a lead structure to avoid breakage at the weld joint.

This object is achieved in accordance with the invention by a strain reliever of the type described above wherein a strain reliever body of the strain reliever has a fastener for fastening the proximal end of the cable lead at a fastening point on the peripheral surface of the body, that is located a distance from the distal end of the body, and wherein the cable is fixed so as to extend in the distal direction from a departure point at the distal end of the body, and wherein the cable process in a helical path on the peripheral surface of the body between the fastening point and the departure point. Thus, by the invention a simple construction is provided for absorbing most of the pulling force in the lead such that the weld is efficiently relieved.

To obtain an efficient absorption of the pulling force by helically winding the lead cable on the peripheral surface of the strain reliever body the cable must be fixed to leave the distal end of the strain reliever body at a specific departure point. In an embodiment of the strain reliever according to the invention a helical groove is therefore formed in the peripheral surface of the body along at least a part of the body length, the groove ending at the departure point at the distal end of the body and the groove is designed for receiving at least a part of the proximal end portion of the cable. By placing the cable in such a groove at the distal end of the strain reliever body the cable will leave the distal end at the outlet of the groove.

According to another embodiment of the strain reliever according to the invention the groove extends from the departure point to at least the fastening point and the fastening point is located in the groove. By applying the cable in a groove on the peripheral surface of the body the cable is held in place on the body in a secure way.

According to yet another embodiment of the strain reliever according to the invention the groove is inclined towards to the distal end of the body by a predetermined angle. This inclination angle can amount to 30 degrees. By having an inclined groove the risk for the cable to creep out of the groove is further reduced. When a pulling force is applied in the longitudinal direction of the cable the cable will be further pulled against the bottom of the groove.

According to another advantageous embodiment of the strain reliever according to the invention the body is made of a stainless alloy, preferably a Co—Ni—Mo—Cr—alloy denoted by a MP35N LT. This is a biocompatible material which is easy to weld and frequently used in this field.

The invention also relates to a lead for an implantable heart stimulator including at least one electric cable having an electric conductor, which lead is provided with the above strain reliever.

DESCRIPTION OF THE PREFERRED EMBODIMENTS

Figure 1:
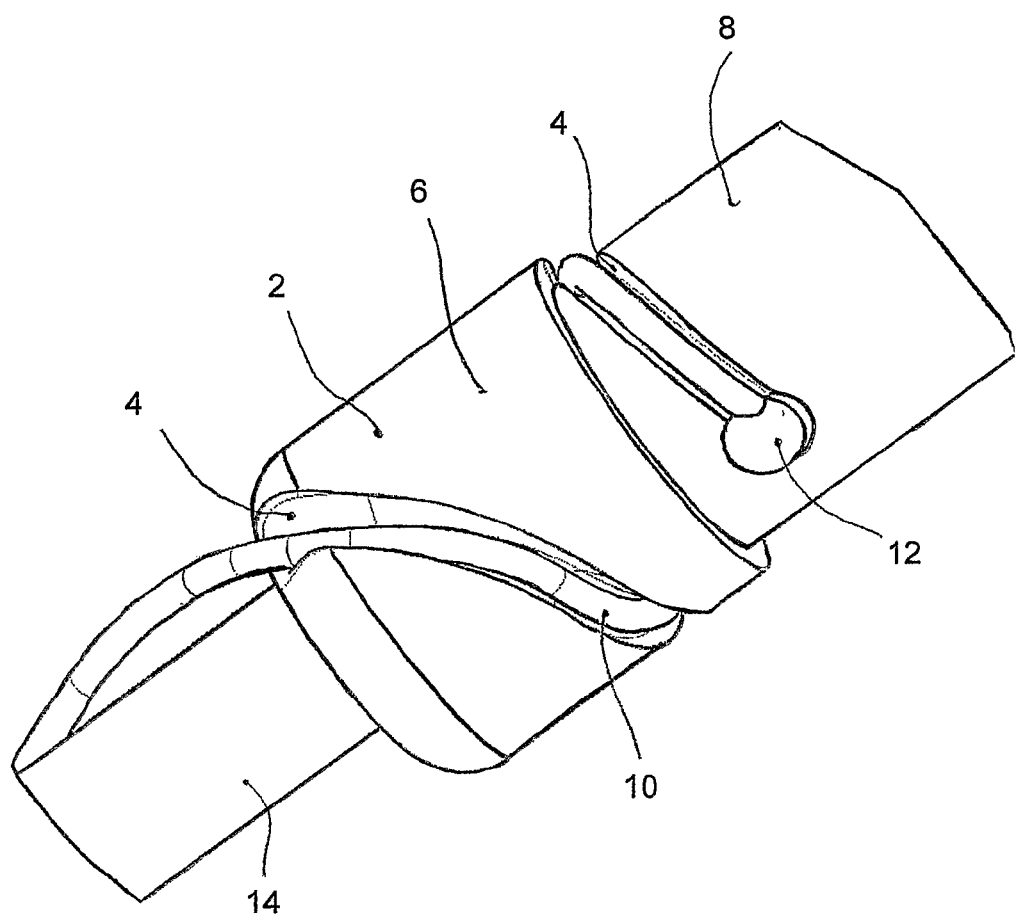
FIG. 1 is a side view of a strain reliever in accordance with the present invention.

FIG. 1 shows an embodiment of the strain reliever according to the invention in a side view. The strain reliever comprises a cylindrical body 2 with a helical groove 4 formed in the peripheral surface. In the shown embodiment the cylindrical body 2 comprises two sections 6, 8 of different diameters. The body 2 is made of an electrically conducting material, like the stainless alloy Co—Ni—Mo—Cr—alloy denoted by MP35N LT. This alloy is biocompatible, well tested in this field and easy to weld.

In the groove 4 a cable 10 of the lead is applied. The cable 10 is fastened to the body 2 at a fastening point at the proximal end of the groove 4 by a weld 12. The cable 10 is extending in the distal direction of the lead from a departure point at the outlet of the groove at the distal end of the body 2.

A connector tube 14 of e.g. silicon is also shown in FIG. 1. This silicon tube forms electric isolation for a possible inner connector coil of the lead.

Figure 2:
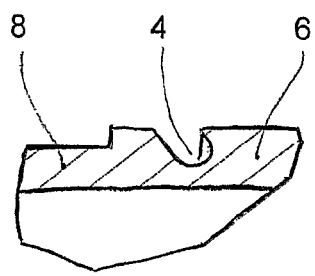
FIG. 2 is a cross-section of the groove in the strain reliever body of the strain reliever sown in FIG. 1.

FIG. 2 shows a cross section of the groove 4. As appears from FIG. 2 the groove is inclined towards the distal end of the body 2 by an inclination angle of 30 degrees. The magnitude of this inclination angle is not critical and can be varied. Also a groove without inclination will held the cable in place.

By locating the cable in a groove in the peripheral surface of the body the cable is held in place on the strain reliever body in a reliable way, and by inclining the groove as illustrated in FIG. 2 the cable is pulled against the bottom of the groove when a pulling force is exerted in the cable in its distal direction, thus further securing the cable in correct position on the body.

As can be seen from FIG. 1 the groove 4 extends a bit more than one turn around the periphery of the body 2.

Experiments have shown that when using a strain reliever of the kind described above in connection with FIGS. 1-2 the pulling force in the lead must be increased from 17 N, as mentioned above, to about 24 N for breaking the weld, i.e. a considerable increase of the breaking strain.

Figure 3:
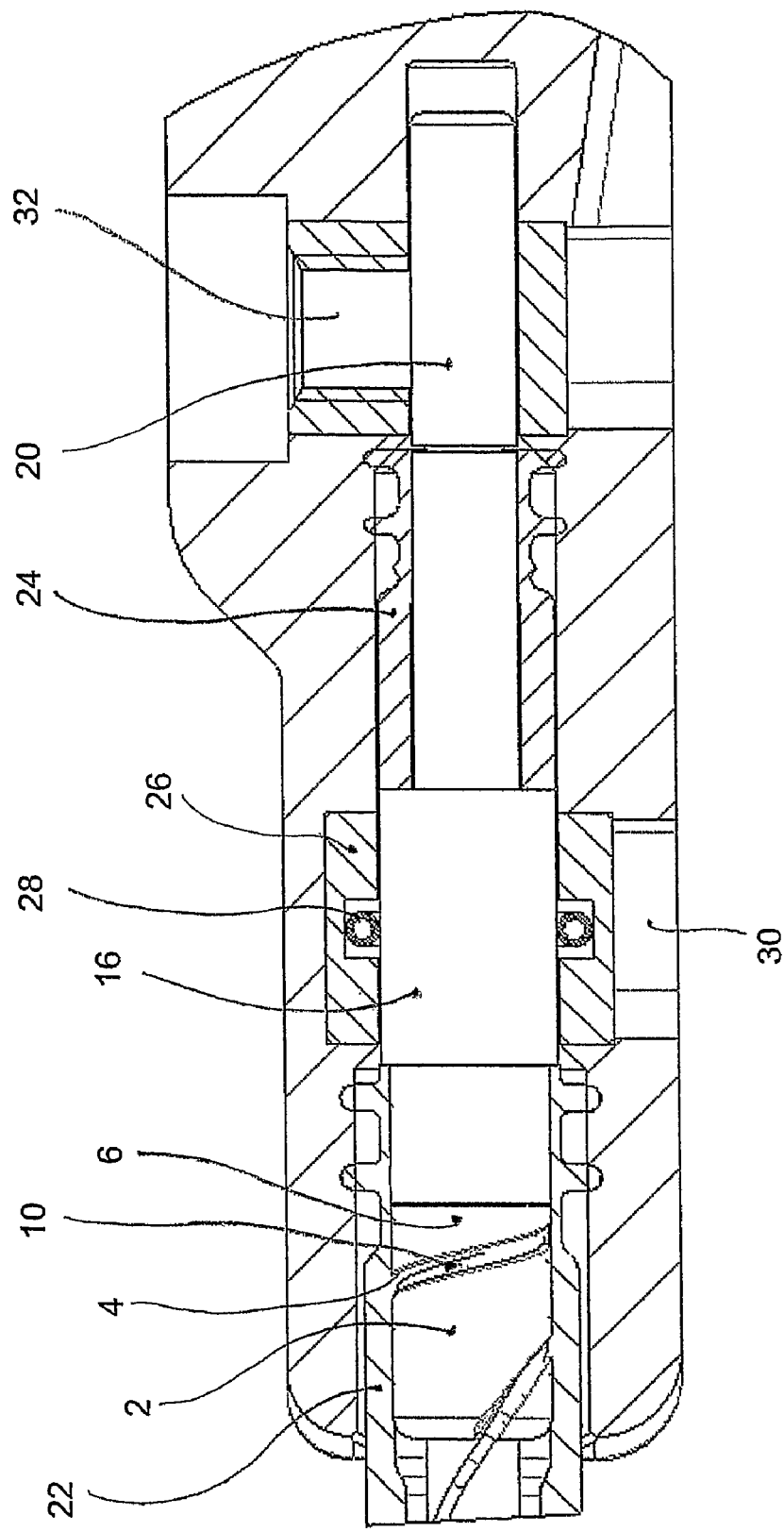
FIG. 3 is a cross section of the header of a heart stimulator with a connected lead provided with a strain reliever according to the invention.

FIG. 3 shows a cross section of the header of a heart stimulator with the proximal end of the lead connected to the header. Although the header is sectioned, the parts of the proximal end of the lead shown in FIG. 1 are not sectioned. The strain reliever body 2 with the cable 10 in the helical groove 4 is shown in the left part of the figure. Section 8 of the strain reliever body 2 is in electrical contact with a connector ring 16, which in its turn is in electric contact with an electrically conducting ring 26 by way of a ringshaped tube 28. A port 30 is provided for connecting the ring 26 to electric circuitry of the heart stimulator.

The strain reliever body 2 is preferably welded to the connector ring 16 to lock the strain reliever body 2 to the heart stimulator header.

A port 32 in the header is shown for screwing a set screw to lock the connector pin 20 to the header and thus complete the connection of the lead in the header.

The connector ring 16 and the connector pin 20 are preferably made of the same electrically conducting, stainless alloy MP35N LT as the strain reliever body 2.

Above an embodiment is described wherein the cable is located in a helical groove in the peripheral surface of the strain reliever body. The strain reliever according to the invention can, however, also be realized by a strain reliever body without such a groove, on which the proximal end portion of the cable is wound around its periphery. The cable is then welded to the body at a fastening point on the peripheral surface a distance from the distal end of the body. At the distal end of the body a means is provided for fixing the cable to extend in the distal direction from a specific departure point at the body distal end. Such a means for fixing the cable to leave the strain reliever body at the departure point can comprise a groove in the peripheral surface of the body extending only along a part of the distance to the fastening point which groove ends at the departure point. By applying the cable in this groove the cable is locked to leave the strain reliever body at the outlet of this groove. Also other means are possible for fixing the cable to extend in the distal direction from the departure point, like a ring attached to the distal end of the strain reliever body at the departure point. Such an embodiment will have an efficient strain reliving effect as well. A pulling force applied to the cable in this embodiment will be transmitted to the strain reliever body by friction between the cable and the peripheral surface of the strain reliever body.

In the above embodiments, the strain reliever according to the invention is described as being constructed for just one cable, but it is evident to those skilled in the art that the strain reliever according to the invention can easily be modified for relieving strains in more than one cable extending in parallel helically around the peripheral surface of the strain reliever body.

Although modifications and changes may be suggested by those skilled in the art, it is the intention of the inventors to embody within the patent warranted heron all changes and modifications as reasonably and properly come within the scope of their contribution to the art.

The invention claimed is:

1. A strain reliever for a lead of an implantable cardiac stimulator, said lead including at least one electric cable having an electrical conductor, said strain reliever comprising:
    a strain reliever body comprising electrically conducting material configured to be in electrical contact with said electrical conductor, said strain reliever body being configured to be locked in electrical contact with electrical circuitry of the cardiac stimulator;
    a fastener configured to fasten said strain reliever body to a proximal end of the cable at a fastening point on a peripheral surface of the strain relieve body located at a distance from a distal end of said strain reliever body; and
    a fixing arrangement at a distal end of said strain reliever body that fixes the cable to extend in the distal direction from a departure point from the distal end of the strain reliever body, and causing said cable to extend in a helical path on a peripheral surface of the strain reliever body between the fastening point and the departure point.

2. A strain reliever as claimed in claim 1 wherein said strain reliever body is substantially cylindrical.

3. A strain reliever as claimed in claim 1 wherein said strain reliever body has a helical groove in said peripheral surface proceeding along at least a portion of a longitudinal length of said strain reliever body, said groove ending at said departure point at said distal end of said strain reliever body, and said groove being configured to receive at least a portion of the proximal end of said cable.

4. A strain reliever as claimed in claim 3 wherein said groove extends from said departure point along a portion of a distance to said fastening point.

5. A strain reliever as claimed in claim 3 wherein said groove extends from said departure point at least to said fastening point, and wherein said fastening point is located in said groove.

6. A strain reliever as claimed in claim 3 wherein said groove is inclined toward said distal end of said strain reliever body by a predetermined angle.

7. A strain reliever as claimed in claim 6 wherein said predetermined angle is 30°.

8. A strain reliever as claimed in claim 3 wherein said groove extends along at least one turn around the periphery of said strain reliever body.

9. A strain reliever as claimed in claim 1 wherein said fastener is a weld.

10. A strain reliever as claimed in claim 1 wherein said strain reliever body is comprised of an electrically conducting stainless alloy.

11. A strain reliever as claimed in claim 10 wherein said strain reliever body is comprised of a Co—Ni—Mo—Cr alloy.

12. A strain reliever as claimed in claim 1 wherein said body is configured to receive multiple, helically proceeding cables substantially in parallel on said peripheral surface between said fastening point and said departure point.

13. A lead for an implantable cardiac stimulator comprising:
    an electrical cable containing an electrical conductor; and
    a strain reliever comprising a strain reliever body comprising electrically conducting material configured to be in electrical contact with said electrical conductor, said strain reliever body being configured to be locked in electrical contact with electrical circuitry of the cardiac stimulator, a fastener configured to fasten said strain reliever body to a proximal end of the cable at a fastening point on a peripheral surface of the strain relieve body located at a distance from a distal end of said strain reliever body, and a fixing arrangement at a distal end of said strain reliever body that fixes the cable to extend in the distal direction from a departure point from the distal end of the strain reliever body, and causing said cable to extend in a helical path on a peripheral surface of the strain reliever body between the fastening point and the departure point.

* * * * *